(12) United States Patent
Feiler et al.

(10) Patent No.: US 7,674,264 B2
(45) Date of Patent: Mar. 9, 2010

(54) PERCUTANEOUS SCAPHOID FIXATION METHOD AND DEVICE

(75) Inventors: Frederic C. Feiler, Colorado Springs, CO (US); Mitchell B. Rotman, Clayton, MO (US)

(73) Assignee: Percutaneous Scaphoid, LLC, Colorado Springs, CO (US)

( * ) Notice: Subject to any disclaimer, the term of this patent is extended or adjusted under 35 U.S.C. 154(b) by 791 days.

(21) Appl. No.: 11/253,162

(22) Filed: Oct. 19, 2005

(65) Prior Publication Data

US 2007/0118116 A1  May 24, 2007

(51) Int. Cl.
*A61B 17/56* (2006.01)
(52) U.S. Cl. .......................... 606/54; 606/96
(58) Field of Classification Search ............. 606/54–59, 606/96–98
See application file for complete search history.

(56) References Cited

U.S. PATENT DOCUMENTS

| 5,591,169 | A  | * | 1/1997 | Benoist .................. 606/59 |
| 6,589,242 | B1 | * | 7/2003 | Feiler .................... 606/56 |
| 6,695,841 | B2 | * | 2/2004 | Feiler et al. ............. 606/54 |

* cited by examiner

*Primary Examiner*—Eduardo C Robert
*Assistant Examiner*—Mary Hoffman
(74) *Attorney, Agent, or Firm*—Richard W. Hanes; Hanes & Schutz, LLC

(57) ABSTRACT

A surgical appliance for assisting in the repair of a fractured bone, such as a scaphoid bone, is disclosed. The device includes first and second adjustably interconnected and spaced apart limb clamping jaws that are transparent to x-ray radiation and are relatively movable toward and away from one another and a rotatable disk carried by the first jaw, said disk having a plurality of bores angularly disposed in the disk for selectively aligning a guide wire to be drilled percutaneously into the fractured bone. Each of the bores are in communication with the space between the first and second jaws and the longitudinal axes of said bores are directed to a common point intermediate the first and second jaws.

6 Claims, 9 Drawing Sheets

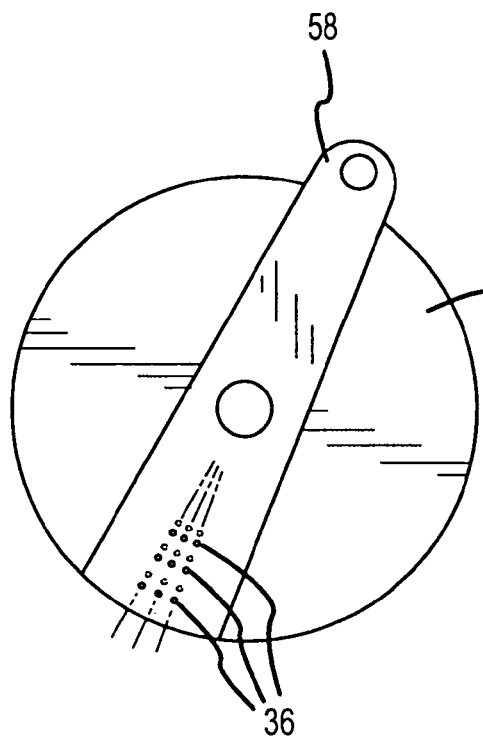
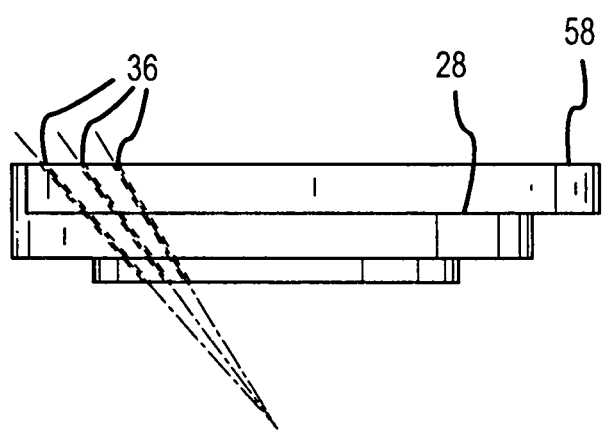
FIG.5      FIG.6
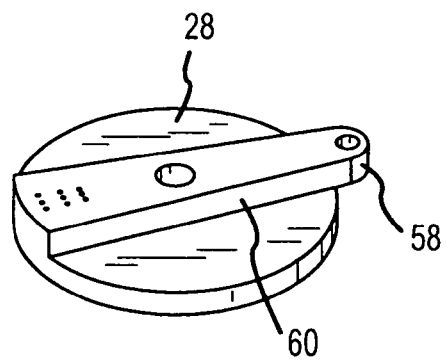
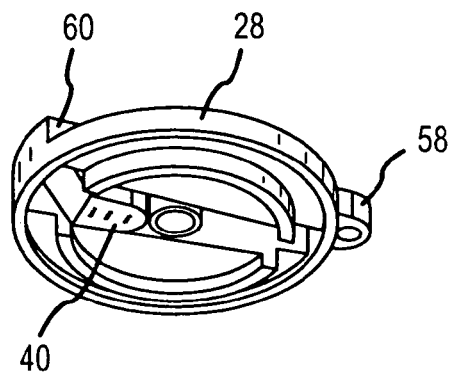
FIG.7      FIG.8

PERCUTANEOUS SCAPHOID FIXATION METHOD AND DEVICE

FIELD OF THE INVENTION

The present invention relates to surgical methods and devices and more specifically to percutaneous fixation of a fractured scaphoid bone in the human wrist.

BACKGROUND OF THE INVENTION

The scaphoid bone in the human wrist is the largest bone of the proximal row of the carpus on the lateral (radial) side, articulating with the radius, lunate, capitate, trapezium, and trapezoid. The scaphoid is surrounded on 80% of its surface by joint fluid containing fibrinolysin, a substance that dissolves blood clots. Because blood clots are necessary for the healing of bone fractures, the substantial presence of fibrinolysin around the scaphoid inhibits healing of a fracture of that bone unless the fracture fragments are fixed in sufficiently good apposition that joint fluid is prevented from entering the fracture site. Failure to properly fix the bone fragments into apposition will result in a non-union because of the presence in the fracture site of joint fluid.

In addition to an undesirable non-union, resulting from poor apposition, a fracture of the scaphoid through its waist often leads to avascular necrosis or death of the distal pole of the bone. This is because the blood supply to the bone is chiefly through the proximal pole and an unhealed fracture at the bone waist cuts off the blood supply to the distal pole, resulting eventually in severe arthritis and deformity of the wrist.

The traditional conservative treatment of a fractured scaphoid includes the application of a cast to the hand and thumb with the hand in radial deviation in an effort to oppose the fracture ends of the bone. Surgical intervention to fix the scaphoid bone typically includes the use of a Herbert screw that requires the expertise of a hand surgeon specialist and results in an extended exposure of the scaphoid bone.

The percutaneous method used with the fixation device of the present invention allows a less experienced hand surgeon or an orthopedist to fix a scaphoid fracture with a screw without the surgical procedures of the past. Such simplification further leads to effectual apposition of the bone fragments and an overall improved result, including the minimization of surgical exposure of the wrist with the attendant increased risk of infection and limitation of wrist movement.

The apparatus of the present invention is an improvement to the fixation and clamping apparatus disclosed in U.S. Pat. No. 6,695,841.

SUMMARY OF THE INVENTION

The present invention provides an improved and novel appliance to advance and further implement the fixation procedure basically described in U.S. Pat. No. 6,695,841. As stated in the said prior patent, the essence of the method is to accurately resolve the required course of a fracture fixation device, such as a screw, and provide means to insure that the fixation device is introduced along that track.

The scaphoid bone is disposed in the wrist at a compound angle that may be demonstrated with anterior-posterior and lateral X-rays or fluoroscopic views of the skeletal wrist structure. This angular position of the scaphoid makes it difficult to insert a fixation device that will follow the desired course into the scaphoid bone without substantial surgical intervention or without the aid of an alignment jig, such as the one of the present invention.

The apparatus of the present invention comprises a clamp, or vise-like device, having a pair of opposed relatively movable jaws between which the wrist containing the fractured scaphoid is inserted for treatment. Upon closing the jaws of the device over the dorsal and palmar aspects of the wrist, the wrist is maintained in a position so that fluoroscopic pictures of the bone may be viewed. From these real time pictures, the desired course of a fixation device may be resolved experimentally by sequentially inserting a guide wire into various ones of a plurality of alignment bores disposed in a rotatable disk carried by the palmar upper jaw of the device of the present invention. By viewing the scaphoid bone and the different bore placements of the guide wire on the monitor of a fluoroscopic X-ray, the bore that most closely positions the guide wire in alignment with the axis of the scaphoid bone is chosen. In addition to the option of having several differently angled bores to choose from, the position over the wrist of any one bore may be varied by vernier position adjustment of the disk. Using the chosen bore to support and direct the guide wire, the wire is drilled through percutaneous tissue and into the scaphoid bone, along the direction and at the angle mandated by the chosen aligning bore.

Once the guide wire is drilled into the bone, the wrist is removed from the clamping vise and a small longitudinal incision is made in the tissue on either side of the guide wire. That tissue is then spread in order to accommodate a drill bit and the subsequently inserted screw. A cannulated drill bit is passed over the guide wire and a hole coaxial with the wire is drilled into the bone terminating near the proximal end of the scaphoid bone. Following removal of the drill, a cannulated screw of appropriate length is passed over the guide wire and screwed into the bone, bringing the fracture fragment faces snugly together in good apposition. The spread tissue is allowed to retract, the guide wire is removed and the incision is closed with one or two sutures.

The bone apposition achieved by the accurately placed and well fitted screw prevents joint fluid from entering the fracture site and dissolving the blood clots that are necessary for bone union.

DESCRIPTION OF THE DRAWINGS

FIG. 5 is a top view of the circular disk that contains the alignment bores. To preserve clarity, depiction of the bottom openings of the bores, in dotted lines, is shown only for the inside set of three bores. Extended from those dotted line depictions of the lower bore openings are dashed lines showing converging trajectory of the axes of those three bores. The axes of the outside three bores and the middle set of three bores converge in a similar manner to that shown for the inside set of three bores.

FIG. 6 is a side view of the circular disk with the alignment bores shown in dotted lines and dashed lines showing the convergence of the axes of the three sets of three bores.

FIG. 7 is a top perspective view of the circular disk that contains the alignment bores.

FIG. 8 is a bottom perspective view of the circular disk.

DETAILED DESCRIPTION OF PREFERRED EMBODIMENT

The bone fracture fixation method and the improved apparatus of the present invention are primarily directed toward treatment of a fractured scaphoid bone in the human wrist. However, the invention can be used in the treatment of fractures in other human or animal bones that present the same challenge in determining and following a proper course for the implantation of a fixation device such as a screw.

The improved percutaneous fixation apparatus of the present invention provides a clamping device to secure the limb having the broken bone while fluoroscopic X-rays are taken and a guide wire is implanted in the bone. Using a fluoroscopic monitor, the position of a guide wire experimentally inserted into selected ones of a plurality of alignment bores is viewed to determine which of the bores aligns the guide wire with the angle of the desired course of a fixation device. The plurality of alignment bores is disposed in a rotatable disk carried by the upper clamping jaw of the device. A guide wire is inserted into the chosen bore which acts to direct the wire as it is drilled into the fractured bone at the desired angle and inclination. Thereafter the guide wire will act as the pathfinder for subsequent procedures, including drilling and implantation of a fixation device into the fractured bone.

Figure 1:
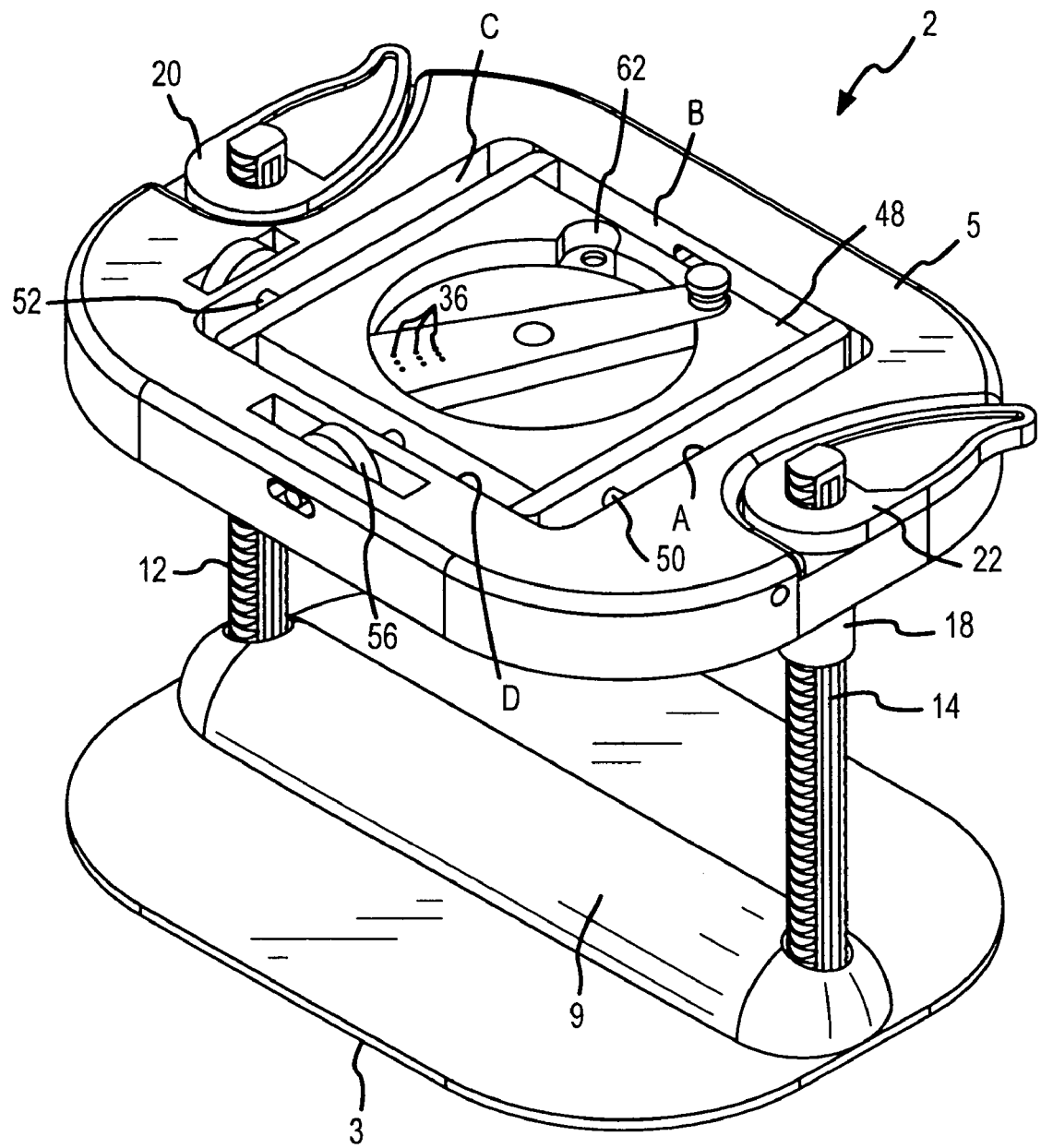
FIG. 1 is a perspective view of the improved scaphoid fixation and wrist clamping device of the present invention.
Figures 2, 2A:
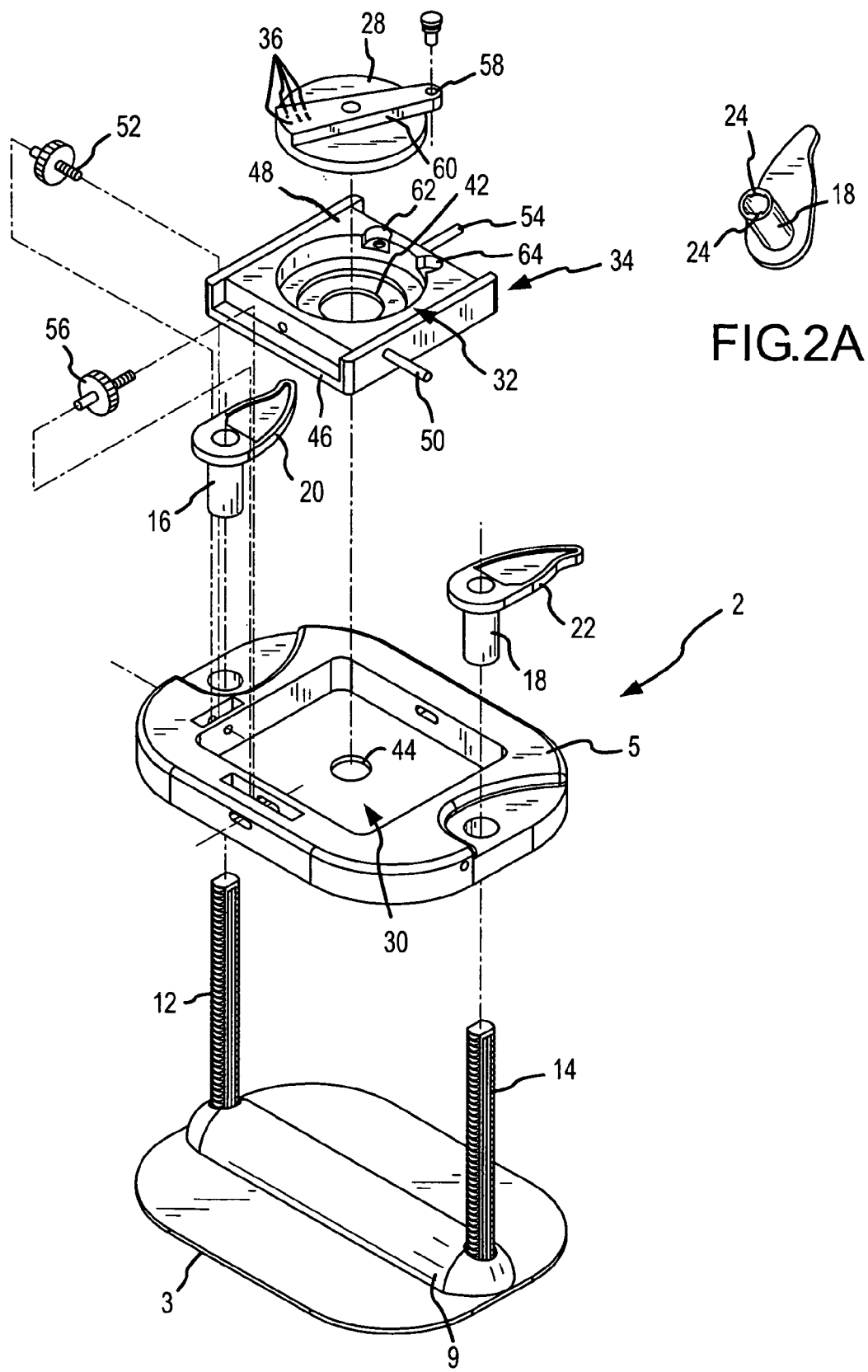
FIG. 2 is an exploded perspective view of the fixation device.
FIG. 2A is a perspective view of the lower end of one of the tubular sleeves that journal the rods that support the upper jaw of the clamping device.

FIGS. 1 through 7 illustrate a preferred form of the improved fixation device 2. Referring first to FIGS. 1 and 2, the fixation device 2 of the present invention comprises a base plate 3 that functions as the lower or dorsal jaw of the clamping apparatus. The opposing jaw 5 may be referred to as the upper or palmar jaw because it contacts the palmar side of the patient's wrist 7 in the clamping position. The dorsal jaw 3 is provided with a laterally oriented raised rib 9 that makes contact with the dorsal side of the wrist to bring its palmar side into proper contact with the lower surface of the jaw 5 when the dorsal and palmar jaws are brought together and locked into clamping position. Positioning the dorsal side of the wrist against, or at least in close proximity, to the lower jaw 3 is important for achieving proper pictures of the wrist and for firmly holding the wrist in a properly fixed position for the later insertion of a guide wire 10.

Figure 3C:
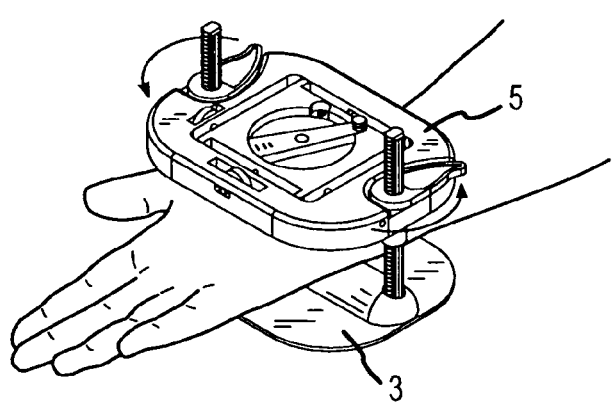
Figure 4:
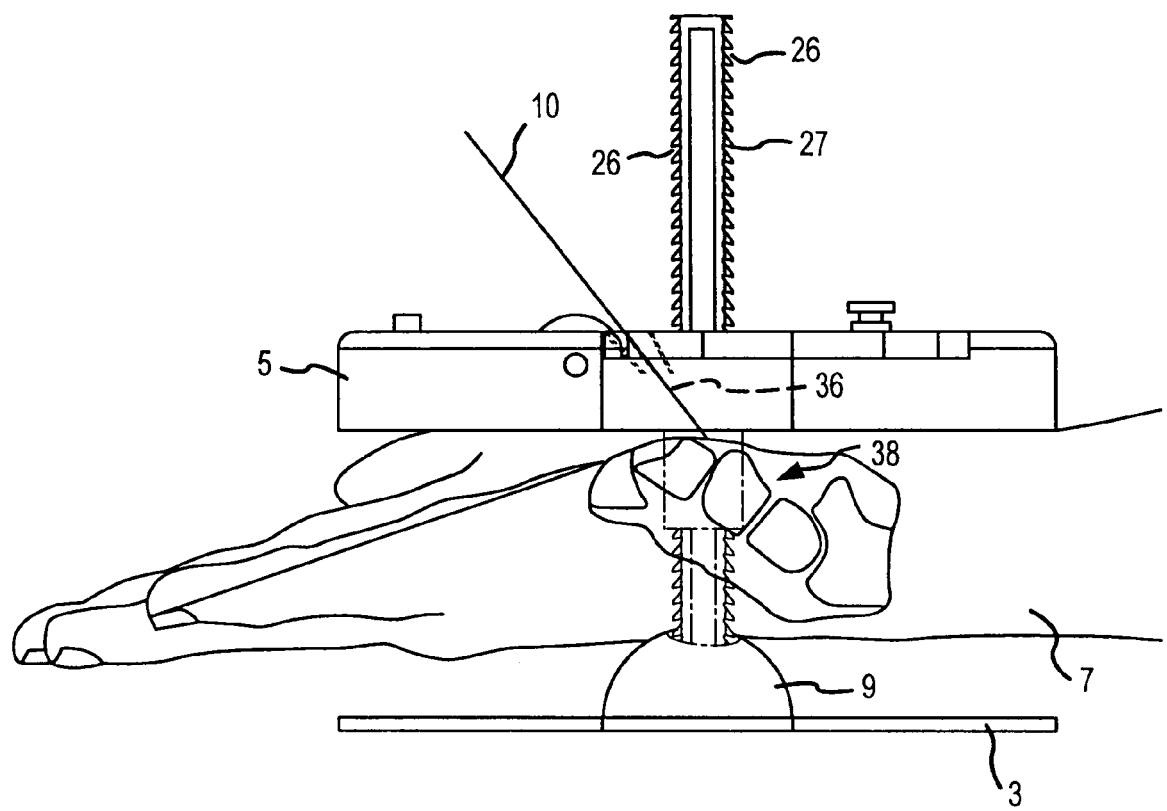
FIG. 4 is a side view of the fixation device clamped around a wrist that is shown as it would appear in a lateral X-ray, demonstrating the position of the fractured and separated scaphoid bone of the wrist.

Secured to the lower jaw 3 are the bottom ends of a pair of upstanding spaced apart partially grooved rods 12 and 14 that support the upper jaw 5. Two opposing sides of the rods are flat and without grooves or teeth. The upper portions of the rods protruding from the base 3 are disposed within tubular guide sleeves 16 and 18 that depend from and are attached to locking levers 20 and 22 positioned over the lateral edges of the top surface of the palmar jaw 5. In order that the upper jaw may slide on the rods for height adjustment and then be locked into position, each of the sleeves 16 and 18 contain a pair of diametrically opposed inwardly extending arcuate sections 24 protruding from the lower inside perimetric edge of each sleeve. In an adjusting, or unlocked position, (FIG. 3B) the inwardly protruding sections 24 of the sleeves face the flat sides of the rods. When the locking levers 20 and 22 are rotated to the locked position (FIG. 3C) the protruding sections 24 engage one of the spaces 26 between teeth 27 on the rods (FIG. 4). Engagement of the protrusions 24 with the teeth 27 prevents the upper jaw 5 from movement along the length of the rods 12 and 14. Rotation of the locking levers to the unlocked position disengages the protrusions from the grooved rods, allowing the upper jaw to be moved freely up or down along the length of the rods.

The parts of the clamping device are constructed from any rigid or semi-rigid material that is transparent to X-ray radiation, such as any number of plastics.

The palmar upper jaw 5 carries the removable and rotatable bore disk 28 within a recess 30 in the upper surface of the jaw. As best seen in FIG. 2, the disk is seated within a circular cavity 32 within a carrier 34 that is adjustably disposed in the recess 30 on the top side of the jaw 5. The purpose of the disk 28 is to provide a base for a plurality of spaced apart and angularly disposed jig bores 36, one of which will be appropriate to receive a guide wire 10. The selected bore will align the guide wire with the axis of the fractured scaphoid bone 38 prior to its being drilled into the bone. The plurality of alignment bores 36 are disposed in the circular disk 28 at a variety of compound angles, one of which will substantially correspond to the compound angle of the axis of the scaphoid bone in the patient. Each of the bores has an individually distinct compound angle and extends from the top surface of the disk 28 to the lower surface 40 of the disk. The lower surface of the disk is exposed to a large opening 42 in the bottom of the carrier 34 and to a smaller opening 44 in the floor of the recess 30 in the palmar jaw.

The plurality of bores 36 are variously angled with respect to the plane of the upper jaw. The horizontal component angles are in the range of 25° to 35° from a vertical sagittal plane through the arm, while the vertical component angles are in the range of 40° to 60° from the palmar plane. This range of angles for the individual bores is exemplary and not to be considered as limiting. The angles and inclination of the disk bores may cover whatever range is required to include a bore that will substantially align the guide wire with the pertinent axis of the scaphoid bone.

It has been found that nine guide wire jig bores placed in an array of columnar groups of three rows, provide a satisfactory number from which to chose a single one that substantially matches the compound angle of the axis of the scaphoid bone in the patient, however, neither the number of bores nor they arrangement is critical. There can be more or less and their arrangement can vary as long as the axes of the plurality of bores converges at a substantially common point in the space between the jaws, that point being the place on the skin of the patient where the guide wire is to pierce the skin. The actual angles of the bores may be whatever is required to substantially align the guide wire with the pertinent axis of the scaphoid bone, considering the bone's inclination with respect to a palmar plane, as seen in a lateral X-ray view of the wrist, and the horizontal angle of the bone with respect to the sagittal plane, as seen in the A-P view of the wrist.

Vernier positioning of one or more of the alignment bores is accomplished by adjusting the position of the disk within the recess. The carrier 34 comprises a channel member 46 having upstanding sides between which is disposed a movable block 48. The channel member is operably interconnected to opposing first and third sides A and C of the recess by a stabilizing stud 50 on which a first side of the channel slides and a threaded thumb screw 52 interconnecting the second side of the channel with the third side C of the upper jaw recess. Rotation of the thumb screw moves the channel laterally back and forth within the recess. The movable block 48 within the channel is interconnected to the opposing second and fourth sides B and D of the upper jaw recess by a similar stabilizing stud 54 and a threaded thumb screw 56. Rotation of the thumb screw moves the block longitudinally back and forth within the recess.

It is apparent that a single set of bores, such as the three groups of three illustrated in the drawings, will function from one position for only one wrist, that is, the left or the right. In the structure disclosed in the prior patent, U.S. Pat. No. 6,695,841, two separate sets of bores were provided, one for the right wrist and one for the left. However, the rotatable disk 28 of the present invention overcomes the need for a structure carrying two sets of alignment bores. The disk carrying the bores is rotatable within its supporting cavity in order that one set of bores 36 will be appropriate for the left wrist when the disk is in one angular position and will be appropriate for the right wrist when the disk is located in a second rotational position. The protruding end 58 of a raised rib 60 on the upper surface of the disk is selectively positioned in one of two detents 62 and 64 in the block 48 that contains the disk. Positioning the rib end 58 into one detent 62 will orient the bores for use on the left wrist while positioning the rib end into the other detent 64 will locate the alignment bores for use on the right wrist.

While the method of percutaneous fixation of the scaphoid bone with the apparatus of the present invention shares many basic steps with the method described in U.S. Pat. No. 6,695,841 the method will again be described to emphasize the simplifications and greater efficiencies achieved with the improved apparatus.

As previously stated, the purpose of the improved accessory device 2 of the present invention is to implement the accurate and effective implantation of a fixation device, such as a screw, across the faces of the fracture fragments of a scaphoid bone without surgically opening the wrist to expose the bone. Maximum apposition of the bone fragments tends to resist the entry of joint fluid into the fracture site, thus eliminating the destruction of the blood clots that are necessary to the union of the bone by the surrounding joint fluid.

Figure 3A:
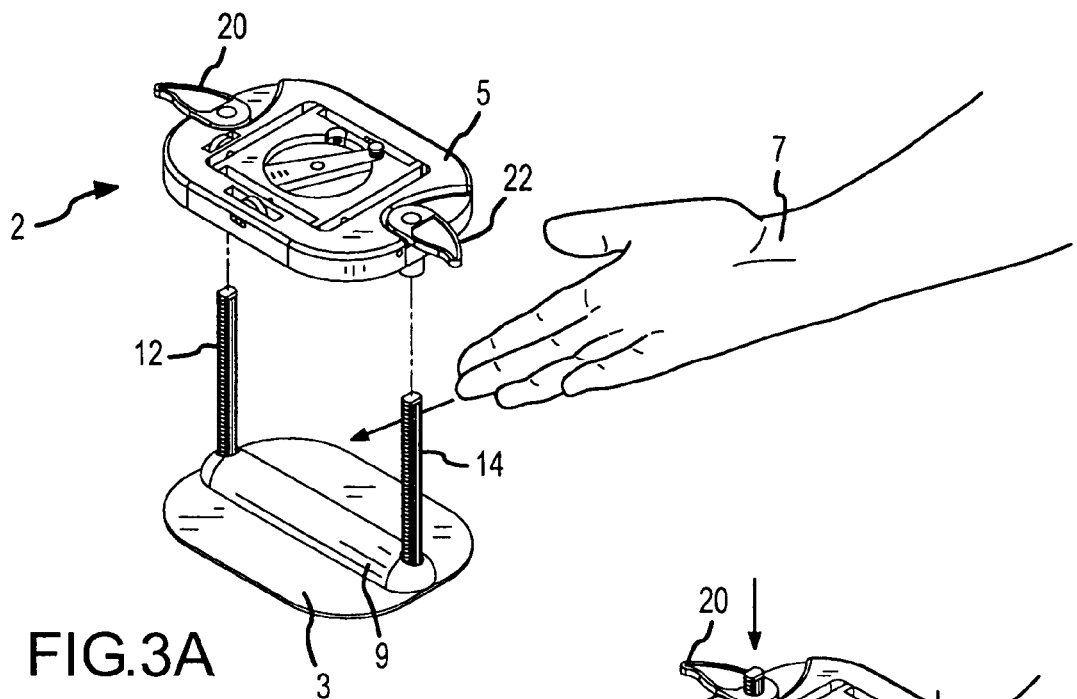
FIGS. 3A, 3B and 3C are perspective views of the fixation device showing the progressive steps of inserting a wrist between the upper and lower jaws of the device, bringing the upper jaw into clamping position and locking the upper jaw in position.
Figure 3B:
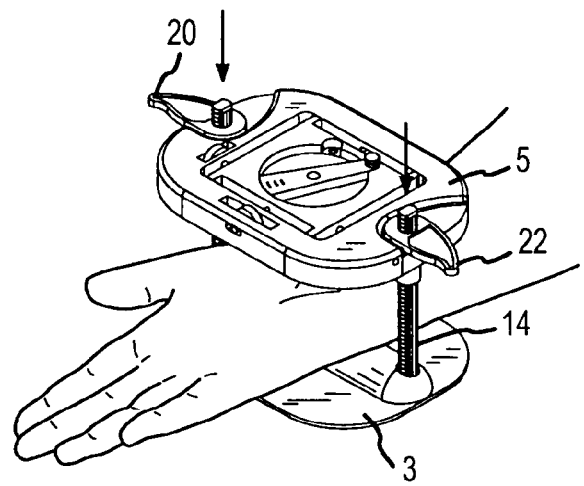

The process begins by placing the dorsal side of the patient's wrist (right wrist in the illustration) over the rib 9 of the base jaw 3 (FIG. 3A). The palmar jaw 5 of the clamping device is positioned on the base supporting rods 12 and 14 (FIG. 3B) and lowered to a wrist clamping position where the locking levers 20 and 22 are rotated to secure the jaw 5 in its clamping position (FIG. 3C).

Figure 10:
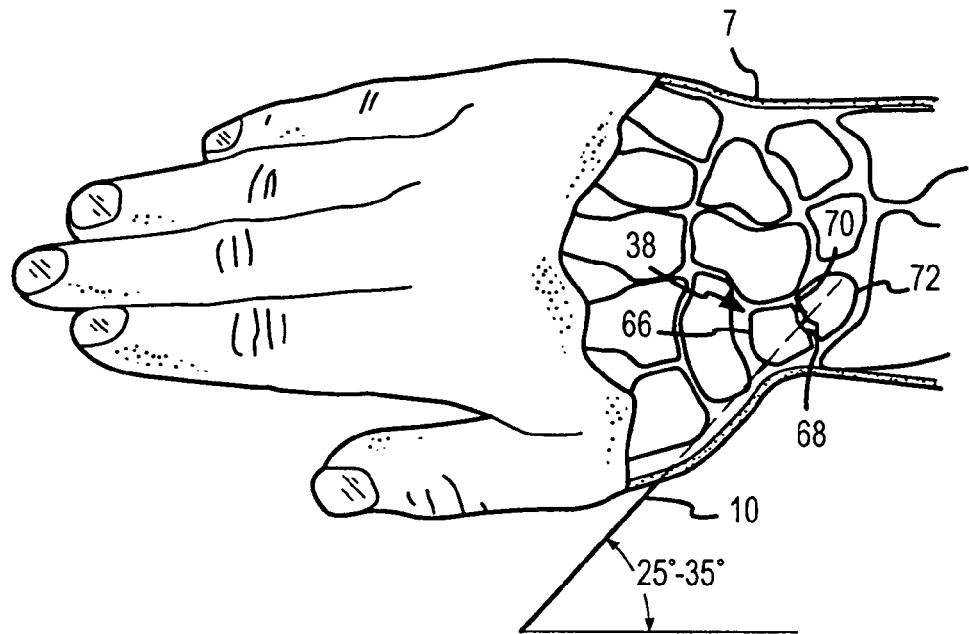
FIG. 10 is an anteroposterior X-ray view of the wrist showing the lateral angle of the scaphoid bone.
Figure 11:
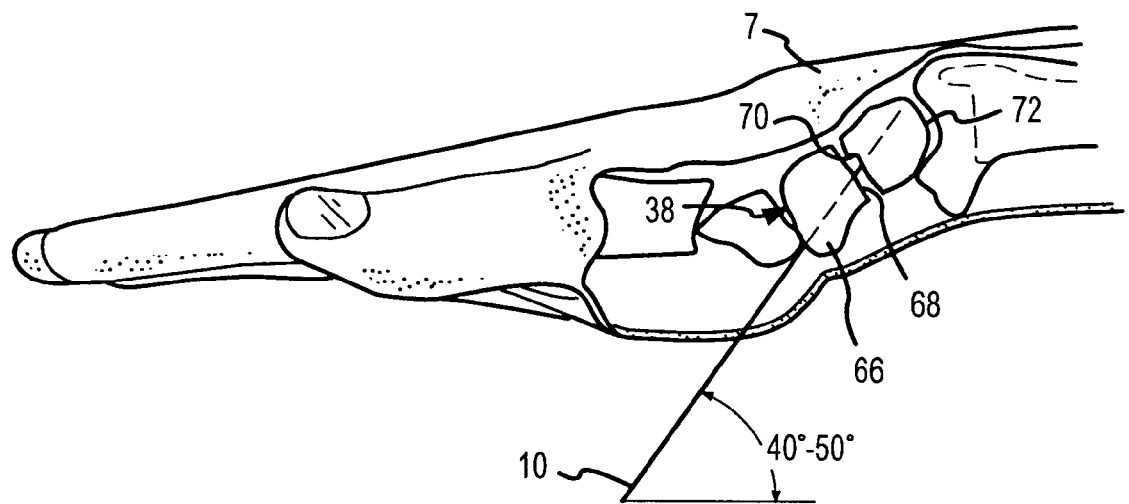
FIG. 11 is a lateral X-ray view of the wrist showing the elevation angle of the scaphoid bone.

Using a C-arm fluoroscope, A-P and lateral views of the clamped wrist are conveyed to a monitor where the surgeon can view an experimental position of a guide 10 wire inserted in one of the jig bores 36 in the rotatable disk 28 that has been positioned in the carrier for work with the right wrist (FIG. 4). The lateral view is used to determine the vertical angle from the horizontal of the scaphoid bone, as shown in FIG. 4 while the A-P view supplies the information for aligning the guide wire laterally. If the guide wire does not align with the axis of the scaphoid bone (as it does not in FIG. 4) the guide wire is tried in a different one of the plurality of alignment bores. The x-y axes vernier adjustment features of the device are employed to finely adjust the position of the circular disk and the alignment bores. When the best bore is found and its position is resolved so as to align the guide wire with the axis of the fractured scaphoid bone, the wire is then ready to be drilled. As shown in FIGS. 10 and 11, the wire 10 is drilled into the wrist tissue, the volar distal pole 66 of the scaphoid bone 38 and across the fracture faces 68 and 70 to the dorsal proximal pole 72 of the scaphoid bone. The guide wire will act as the pathfinder for subsequent fixation steps. For a very proximal fracture of the scaphoid bone, it may be desirable to place the fixation screw into the scaphoid bone from its proximal end towards the distal end. This can easily be done with the present device by drilling the previously placed guide wire in the scaphoid bone out of the skin proximally with the wrist flexed to about 85° before using the drill, but after measurement of the needed fixation screw. The procedure then is the standard procedure for use of a percutaneous fixation screw.

Once the guide wire is drilled into the bone the function of the apparatus of the present invention has been served and the patient's wrist is removed from the clamping device.

Figure 9:
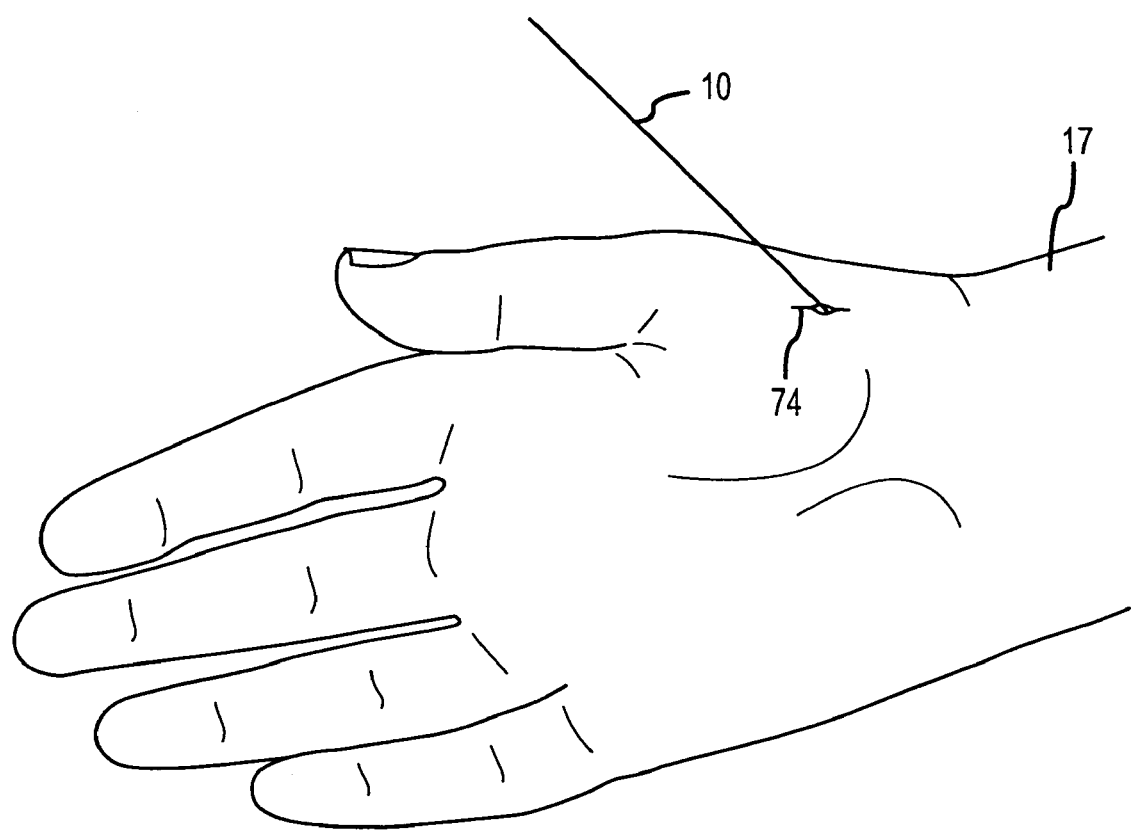
FIG. 9 is a palmar view of the hand and wrist showing the guide wire inserted through the small incision in the wrist tissue that is necessary to accommodate the drill and fixation device.
Figure 12:
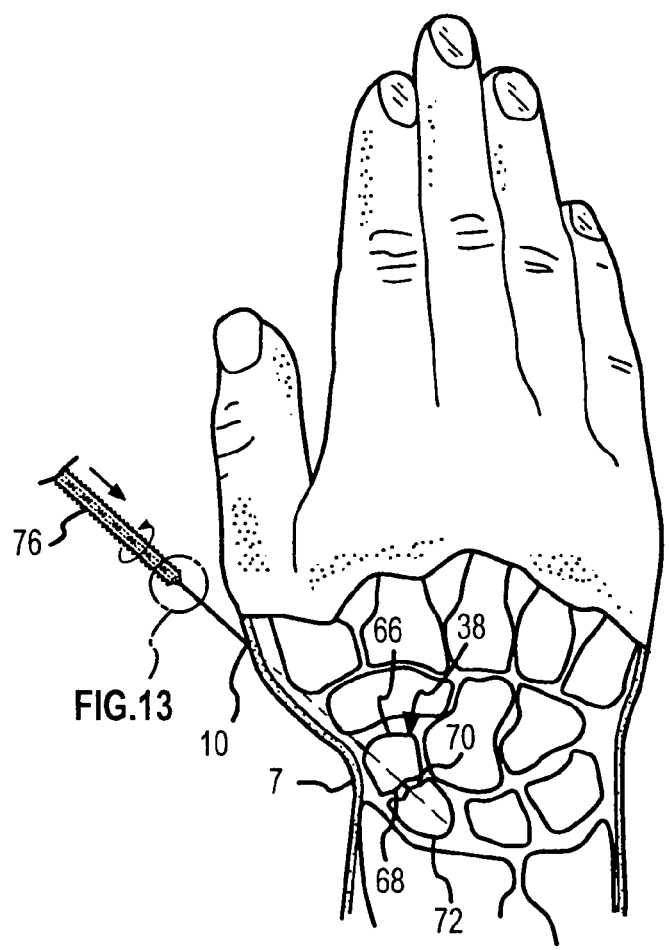
FIG. 12 is an anteroposterior view of the wrist showing a cannular drill bit being directed in its proper course by the guide wire that has been previously drilled into the scaphoid bone.
Figure 13:
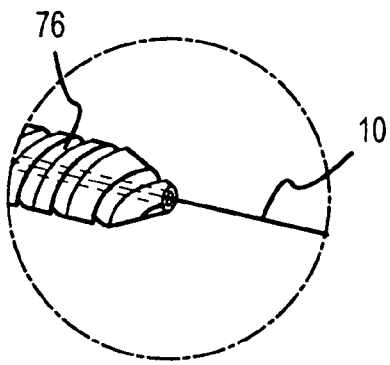
FIG. 13 is an enlarged view of the tip end of the cannulated drill bit of FIG. 12.
Figure 15:
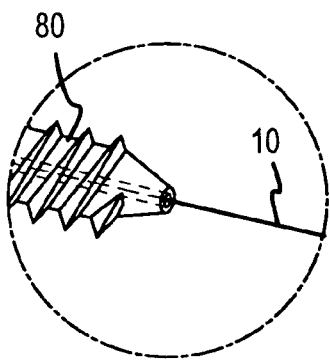
FIG. 15 is an enlarged view of the tip end of the cannulated fixation screw of FIG. 14.
Figure 14:
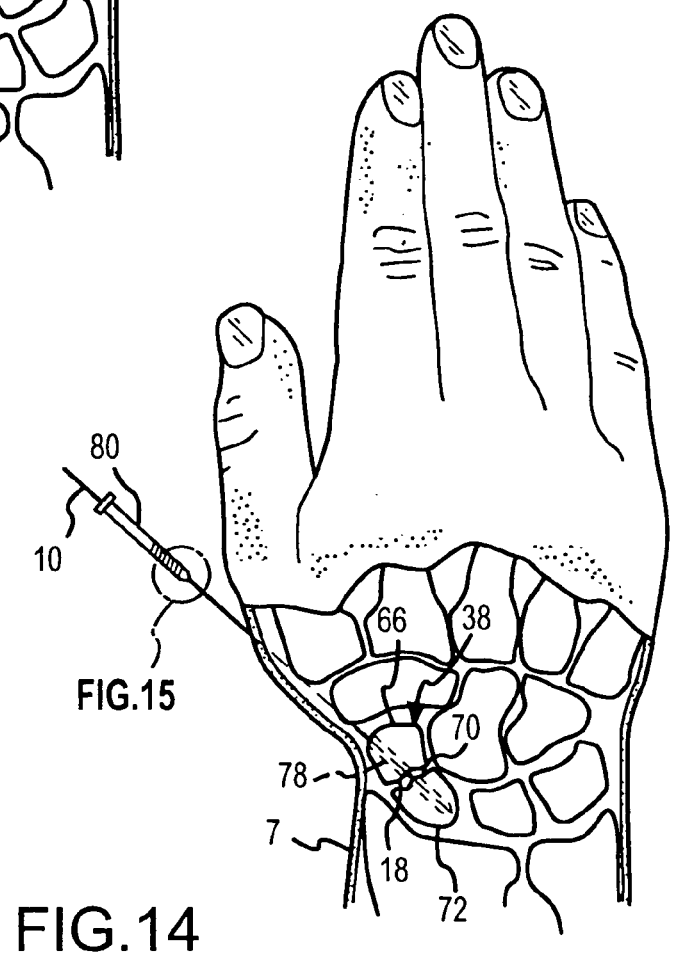
FIG. 14 is a anteroposterior view of the wrist showing a cannular fixation screw being directed in its proper course by the guide wire that has been previously drilled into the scaphoid bone.
Figure 16:
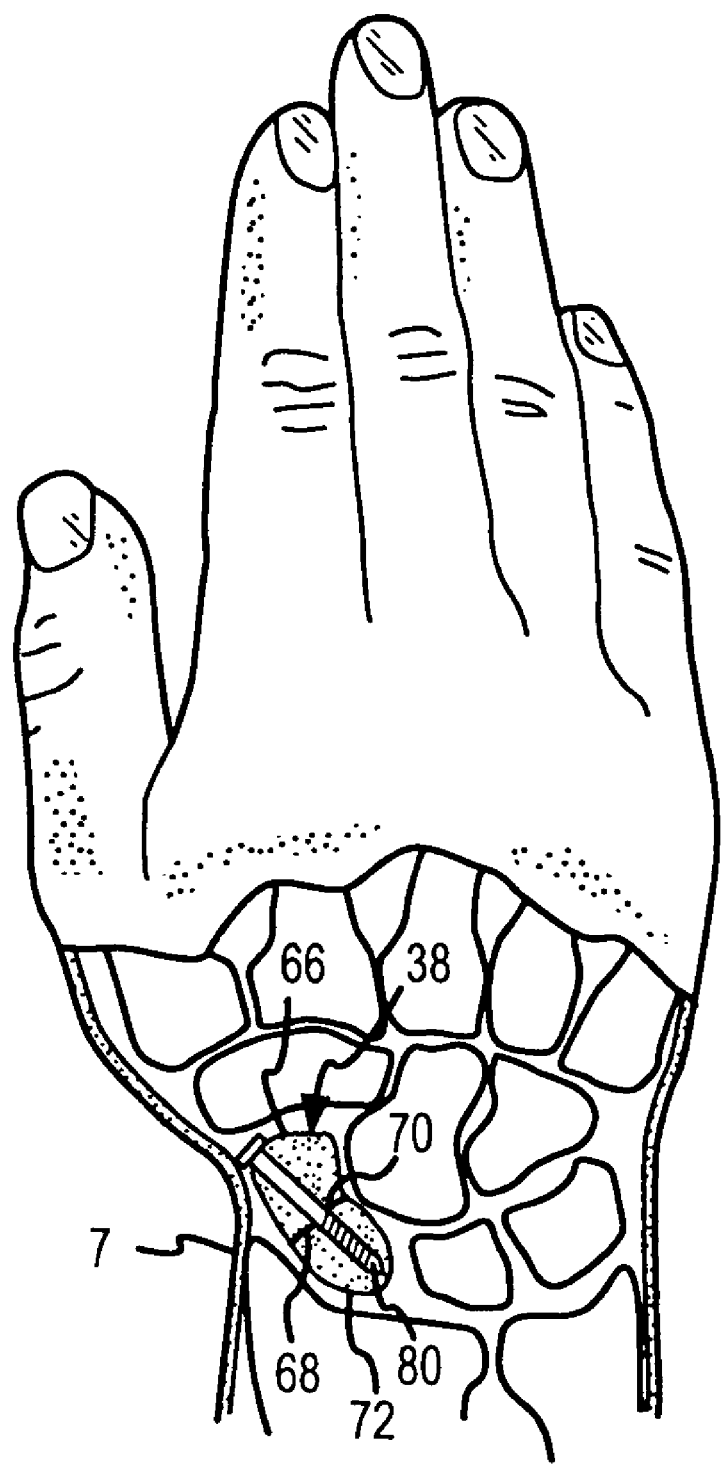
FIG. 16 is a anteroposterior view of the wrist showing a fixation screw in place in the fractured scaphoid bone, having brought the separated pieces of the bone together.

A small longitudinal incision 74 is made proximally and distally on either side of the guide wire 10, as illustrated in FIG. 9. A hollow tissue spreader (not shown) is passed over the guide wire 10 and pressed into the incision. The spreader is carefully pushed into the incision until its end impinges on the scaphoid bone, pushing aside important structures in this area, including the radial artery and its accompanying veins and the terminal sensory branch of the radial nerve that gives sensation to the thumb. Next, as shown in FIGS. 12 and 13, a cannulated drill bit 76 is passed over the guide wire and through the opening prepared in the tissue by the spreader. Following the guide wire, the drill bit 76 drills a hole 78 in the scaphoid bone along the desired course of the fixation device around the guide wire. The hole is of sufficient diameter and length to accommodate a fixation device, such as a screw 80 (FIGS. 14-16). After the drill bit is withdrawn, the cannulated screw 80 is passed over the guide wire and screwed into the bone 16, as shown in FIGS. 14 and 15. When the screw has been fully seated and the bone fragments are pulled together in apposition (FIG. 16), the tissue spreader and the guide wire are removed and the small incision is closed with one or two sutures.

Employment of the improved apparatus and the method of the present invention results in good apposition of the bone fragments with reasonable assurance that a union of the fragments will take place, since joint fluid has been isolated from the fracture site.

What is claimed is:

1. In a surgical appliance for repairing fractures of the scaphoid bone in a human wrist having vise means comprising upper and lower spaced apart jaws that are transparent to x-ray radiation and are relatively movable toward and away from one another for retaining there between at least a portion of a human wrist and means interconnecting the upper and lower jaws for selectively fixing the spacing between the jaws, the improvement comprising, a recess in the upper jaw having a floor with a central opening therein, a mounting block adjustably disposed in the upper jaw recess, said block having a circular cavity therein that is superimposed over the recess floor opening and having a peripheral annular flange, a circular disk removably disposed in the circular cavity and supported for rotation therein by the peripheral annular flange, and a plurality of bores angularly disposed in the circular disk, the longitudinal axes of said bores being all directed to the opening in the recess floor.

2. A surgical appliance for use in repairing a fractured bone in a limb, comprising first and second spaced apart jaws that are transparent to x-ray radiation and are relatively movable toward and away from one another, means interconnecting the first and second jaws for selectively fixing the spacing between the jaws and clamping there between at least a portion of the fractured limb, a rotatable disk carried by the first jaw, a plurality of alignment bores each having a longitudinal axis angularly disposed in the disk, each of which bores are in communication with a space between the first and second jaws and where longitudinal axes of said bores are directed to a common point intermediate the first and second jaws.

3. The appliance of claim 2 and further including means carried by the disk for limiting the rotation of the disk to one of two selectable positions.

4. The appliance of claim 2 and further including adjustment means operable on the disk to regulate its lateral and longitudinal position relative to the first jaw.

5. The appliance of claim 4 where the adjustment means include, movable carrier means for housing the disk, said carrier means having X and Y axes, rotatable threaded screw means operably interconnecting the X and Y axes of the carrier means with the first jaw.

6. The appliance of claim 2 where the alignment bores are arranged in an array of columns and rows.

\* \* \* \* \*